United States Patent
Majewski et al.

(10) Patent No.: US 8,049,176 B1
(45) Date of Patent: Nov. 1, 2011

(54) METHOD AND APPARATUS FOR REAL TIME IMAGING AND MONITORING OF RADIOTHERAPY BEAMS

(75) Inventors: Stanislaw Majewski, Yorktown, VA (US); James Proffitt, Newport News, VA (US); Daniel J. Macey, Birmingham, AL (US); Andrew G. Weisenberger, Yorktown, VA (US)

(73) Assignee: Jefferson Science Assocates, LLC, Newport News, VA (US)

( * ) Notice: Subject to any disclaimer, the term of this patent is extended or adjusted under 35 U.S.C. 154(b) by 0 days.

(21) Appl. No.: 12/316,444

(22) Filed: Dec. 12, 2008

(51) Int. Cl.
  *G01T 1/16* (2006.01)
(52) U.S. Cl. ............ 250/363.1; 250/363.05; 250/363.08
(58) Field of Classification Search ............... 250/363.1, 250/363.05, 363.08
  See application file for complete search history.

(56) References Cited

U.S. PATENT DOCUMENTS

| | | | | |
|---|---|---|---|---|
| 3,011,057 A | * | 11/1961 | Anger | 250/366 |
| 3,209,201 A | * | 9/1965 | Anger | 315/9 |
| 5,033,075 A | * | 7/1991 | DeMone et al. | 378/156 |
| 5,838,009 A | * | 11/1998 | Plummer et al. | 250/363.05 |
| 6,969,194 B1 | * | 11/2005 | Nafstadius | 378/197 |

OTHER PUBLICATIONS

Min et al., "Prompt gamma measurements for locating the dose falloff region in the proton therapy." Applied Physics Letters, vol. 89 (2006) pp. 183517-1 to 183517-3. Published by AIP on Nov. 2, 2006. <doi:10.1063/1.2378561>.*

* cited by examiner

*Primary Examiner* — Constantine Hannaher

(57) ABSTRACT

A method and apparatus for real time imaging and monitoring of radiation therapy beams is designed to preferentially distinguish and image low energy radiation from high energy secondary radiation emitted from a target as the result of therapeutic beam deposition. A detector having low sensitivity to high energy photons combined with a collimator designed to dynamically image in the region of the therapeutic beam target is used.

4 Claims, 2 Drawing Sheets

METHOD AND APPARATUS FOR REAL TIME IMAGING AND MONITORING OF RADIOTHERAPY BEAMS

The United States of America may have certain rights to this invention under Management and Operating Contract DE-AC05-06OR23177 from the United States Department of Energy.

FIELD OF THE INVENTION

The present invention relates to methods and apparatus for imaging and monitoring the delivery of therapeutic radiation beams and more particularly to in-situ/in-vivo tracking of these beams.

BACKGROUND OF THE INVENTION

Different types of radiation therapy beams, including electron beams, gamma rays, high energy X-rays and protons are used in the treatment of various cancer states. Verification of the location and magnitude of the radiation dose delivered to target volume in the body in such treatments is an important requirement and in-situ/in-vivo tracking of these beams is an important challenge for radiation therapy today.

While radiation therapy procedures are very carefully planned, specifically addressing a selected target volume in each patient, and each radiation session planned using available simulation tools and prior experimental clinical data, there is no standard technique available at this time to provide real time monitoring and assurance that the procedure is indeed delivering the desired/lethal dose to the cancer tissue, while sparing the neighboring organs and tissues that might be at risk.

There thus remains a need for a method for verifying the location and magnitude of the radiation dose delivered to target volume in the body in such treatments as well as for the in-situ/in-vivo tracking of these treatment beams.

OBJECT OF THE INVENTION

It is therefore an object of the present invention to provide a method and apparatus for real time imaging and monitoring of radiotherapy beams.

SUMMARY OF THE INVENTION

A method and apparatus for real time imaging and monitoring of radiation therapy beams is designed to preferentially distinguish and image low energy radiation from high energy secondary radiation emitted from a target as the result of therapeutic beam deposition. A detector having low sensitivity to high energy photons combined with a collimator designed to dynamically image in the region of the therapeutic beam target is used.

DETAILED DESCRIPTION

Figure 1:
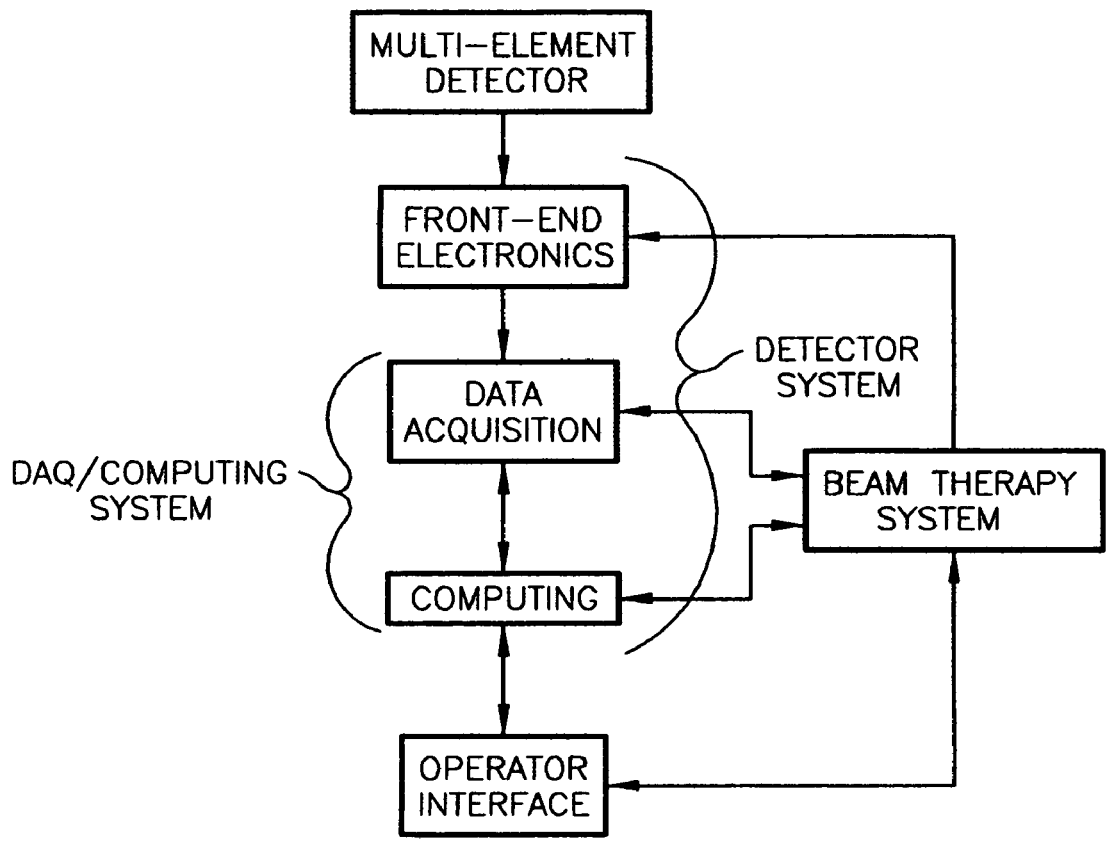
FIG. 1 is a detector system data flow diagram.

As a result of energetic multi-MeV radiation beams interacting with the tissue/bone target, as occurs during brachytherapy treatment, different excited nuclear states are produced with the highest representation from species produced from naturally occurring nuclei in the organic target such as Oxygen, Carbon, etc. Some of these excited states de-excite with prompt emission of characteristic high energy gamma rays. These signature gamma lines can be used to identify the specific excited species and to study and establish the correlation between the emission of these gamma lines and therapeutically relevant energy deposit in the target.

However, imaging these multi-MeV gamma lines is very difficult because collimators must be used to produce meaningful images of the beam in the target area.

In the recent study (Chul-Hee Min et al., "Prompt Gamma Measurements for Locating the dose Falloff Region in ProtonTherapy", Applied Physics Letter 89, 183517, 2006) it was shown that the prompt gammas generated by nuclear reactions can be used to verify the proton range in proton radiation therapy. The very limited angular coverage radiation detector used in that study was optimized for detection of characteristic gamma lines above 4 MeV and had to be scanned along the proton beam direction to establish distribution of the intensity of the selected gamma emissions along the beam path. While this method enabled execution of the pilot research study, that approach and apparatus would not be practical in clinical situations, especially when dealing with dynamically moving or scanning beams. However, the study demonstrated that verification of the proton range (position of the distal falloff) by the prompt gamma measurements is expected to be clinically useful for ensuring the tuning of proton energy and the ranges computed from the treatment planning.

The above study provided the initial proof of principle that with the properly designed (imaging) detector, position and range of the radiation beam can be dynamically monitored to provide immediately available useful feedback information on the progress of the therapy.

By making the detector "blind" to high energy gamma radiation emitted from the target it has been found possible to produce images of the beam by employing the relatively simple pinhole collimator concept.

According to the present invention, a similar simple imaging approach can be designed to image the gamma radiation beams, which are predominantly currently used in radiation treatment, during their interacting with the target. However, the major difference related to the gamma beams is that they do not deliver the same sharp characteristic increase in the radiation dose deposit as in the case of proton or ion beams at the end of their range in tissue (at the end of Bragg curve). The novel imaging concept described herein reduces the effects of large angle scatter and provides real time images of the gamma beam with adequate sensitivity and spatial resolution.

While the authors of the above-referenced publication have demonstrated that good 1 mm-range spatial correlation exists between the position of the maximum of deposited energy in the target (corresponding to the stopping proton beam) and the measured distribution of characteristic multi-MeV gamma emissions along the beam track, spatial distribution of the lower mostly secondary radiation (Compton scattered gamma, bremstrahlung, X-rays, etc) blurs the image of the initial energy deposit. However, there is a direct relationship between the shape and size of the blurred "beam image" obtained in this low radiation energy range and that the initial position of the static or moving beam that can be unfolded with the desired 1 mm type resolution.

In the case of ion carbon beams, for example, it has been observed that production of positron emitting radionuclides such as O-18, C-11, N-14, etc are highly correlated with the distribution of the delivered biologically relevant therapeutic radiation dose. Positron radiation induced in the target tissue can be imaged with modified and adapted standard PET scanners and that this distribution can be compared to predicted or calculated distributions as a measure of how precisely the radiation dose is delivered.

For proton beams, the correlation between the pattern of energy deposition (related to the so-called Bragg curve distribution) and the density of the resultant positron emitters is less spatially correlated than for ion beams, with a shift of positron sites distribution up-stream compared to the therapy dose distribution. Therefore, this situation requires more involved physical process modeling or simulation to achieve meaningful control and guidance information from the PET scan.

In addition, while not imaged in-situ, in this case there is also possible to use standard PET or PET/CT scanners to provide good quality feedback information. In such a scenario the patient is imaged promptly post therapy and the information is used to assess progress and to plan the next therapy session.

Figure 3:
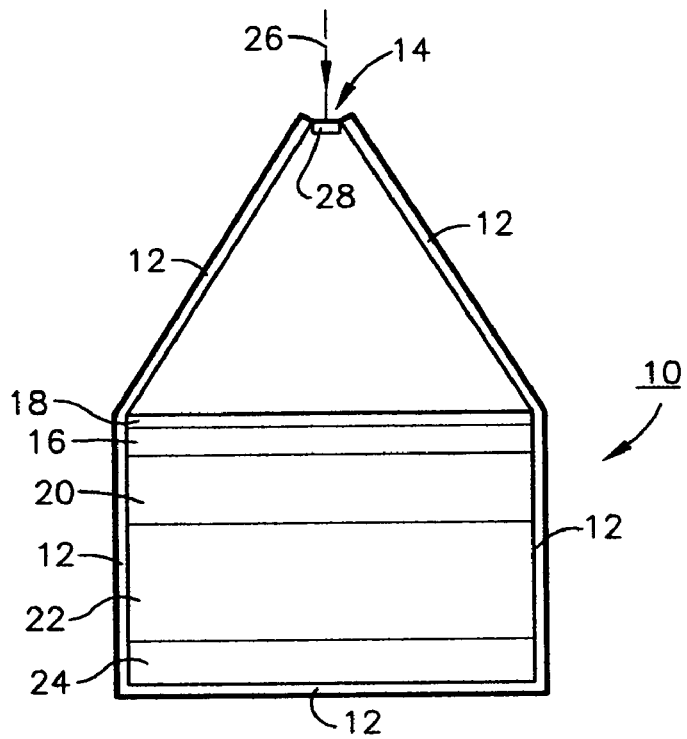
FIG. 3 is schematic depiction of a detection module with a single pinhole collimator.

Referring now to the accompanying drawings, as shown in FIG. 3, the detection module 10 of the present invention comprises: a) a radiation shielding housing 12; b) a pinhole collimator 14; c) a radiation sensitive layer 16; d) preferably a protective cover 18 over radiation sensitive layer 16; e) a photodetector 20; f) readout electronics 22; and g) a power supply and communication electronics 24 as described below.

In operation, low energy radiation 26 emitted from the region where a therapeutic beam strikes a target (not shown) reaches radiation sensor 16 via pinhole collimator 12 that may be equipped with a filter 28 of the selected lowest part of the incoming photon spectrum. On board electronics 22 convert the radiation events to electronic signals with encoded spatial positioning of the detected radiation. The data acquisition system (DAQ), located on board the imager and/or at a distant electronics box or cabinet where computer is located, converts the flow of radiation detection events into digital data that in turn is converted by the data processing software to dynamic images of the beam for immediate display. These relationships are depicted graphically in process the process flow diagram of FIG. 1.

Detection module 10 of the present invention can exhibit, for example, the following general parameters: a field of view (FOV) in the target region of from ~5 cm to ~50 cm to cover most of the useful radiation treatment fields; spatial resolution of from about 1 mm to 1 cm, depending on the imaging task; the ability to display on-line beam projections in the target volume in 3D with ~10 msec time resolution; and the ability to store dynamic imaging data for further off-line processing for more accurate evaluation of the therapy session Different radiation sensors 16 can be employed in the imagers of the present invention, with three major families of usable sensors: those based on solid state materials such as silicon, CdZnTe, CdTe, GaAs, HgI2, etc. structured as continuous plates or pixellated arrays, with direct radiation detection and electronic signal creation in the same sensor; those based upon scintillation films, layers, plates, or pixellated arrays in which radiation is converted to scintillation light and then in the second step into electronic signal, resulting in a two-step detection process; and those based on microchannel plate (MCP) electron multipliers without or with an additional sensor layer coupled to it (MCP has intrinsic low sensitivity to radiation).

The scintillation basedradiation sensors requires a photo-detection device to convert the scintillation light into an electronically processable signal that ultimately leads to the creation of a dynamic image of the scanning beam during treatment.

Some examples of useful scintillator sensor materials include: organic liquid (radiation hard) or plastic scintillators; X-ray scintillation screens such as gadolinium oxysulfate; ceramic scintillators; glass scintillators; inorganic scintillators such as NaI(Tl), CsI(Tl), CsI(Na), GSO, LaBr3, LSO, LYSO, YAP, YAG, BGO, CaF2(Eu), CdWO4, BaF2, CsF, ZnS(Ag); and powders or mixtures with epoxies etc. of inorganic scintillators.

Examples of useful photodetector technologies in accordance with the present invention include: single PMTs or arrays of standard PMTs or multielement PMTs (such as Photonis XP1470); single or arrays of position Sensitive PMTs such as 1" Hamamatsu model R8520-00-C12 or 2" models H8500 and H9500, or Burle 2" models 85011 and 85021 based on microchannel plates; silicon Avalanche Photodiodes or the novel Silicon Photomultipliers (for example from SensL); and microchannel plates not included in the PMT structure but coupled by the user to a scintillation sensor to form a new detector.

Pinholes can be made from the usual set of typically high Z high and high density metals or compounds having composition comprising a large percentage of these metals: lead (Pb), tungsten (W), gold (Au), depleted Uranium, etc.; tungsten alloys and tungsten epoxy mixtures with tungsten powder; and lead alloys.

The pinholes can be additionally equipped with insert filters 28 to filter out part of the incoming gamma, X-ray etc. spectrum to optimize overall imager response. Typically filters will be single or multi-component plugs made of lower Z material such as the following metals: Al, Cu, Ni, etc., and their alloys but can also be made of mixtures of other materials.

In principle, pinholes can be of any shape, with round being the most typical, but they may also be square, hexagonal, and even slit forms. The hole can of a gradually changing diameter (such as "knife-edge" type conical shape) or have a cylindrical central part with one or two conically shaped regions below and/or above the cylindrical hole.

Pinhole sizes or diameters will be typically in the range of a fraction of a millimeter (for example 0.5 mm) to few millimeters (for example 5 mm), depending on the type of the imaged beam (ion, proton, or gamma), and required spatial resolution and sensitivity for a particular imaging task.

To increase system sensitivity, multi-pinhole schemes can be implemented, following examples from commercial gamma imaging systems used for example in small animal imaging systems. However, while increasing the system efficiency by effectively opening the collimator diaphragm, such a system requires special reconstruction software which effectively can prevent obtaining immediate feedback on the beam position.

Pinhole sets or arrays can be made from a few to many pinholes, with the limit defined by the system software's capability to reconstruct information obtained from different potentially overlapping projections of the beam image on the detector sensor's surface. Each pinhole will produce its own image projection.

Pinholes will be typically mounted in inserts or as inserts in the radiation shield material placed in front of the imager. The shield's role is to stop radiation that would otherwise strike the radiation sensor material. The shield material, typically lead, tungsten, or alloys of lead or tungsten, is placed in front, but also around, at sides and at the back, of the sensor. The shield will not stop all radiation, especially the highest energy part of the produced gamma or Bremstrahlung spectrum, but it is designed to stop most of the relevant radiation of a kind to which the radiation sensor is sensitive.

As alluded to hereinabove, the novel element of the present invention is the combination of the selected low energy sensitivity of the radiation sensor with the low energy collimation function of the employed pinhole collimator or collimator array.

The characteristic feature of pinhole imaging is that by changing the distance from the pinhole to the target and from the pinhole to the detection surface, parameters such as sensitivity, spatial resolution and magnification factor undergo change. It is possible to vary or scale down or up the actively monitored FOV (and associated spatial resolution) by changing magnification factor.

A preferred system in accordance with the present invention has a set of exchangeable pinholes with differing diameters to change/tune system sensitivity and resolution according to a particular task of imaging tissue or organ during the particular radiotherapy session.

Typically, the pinhole distance to target and the magnification factor will be adjusted before the therapy session to match the requirements of the specific irradiation task.

Figure 2:
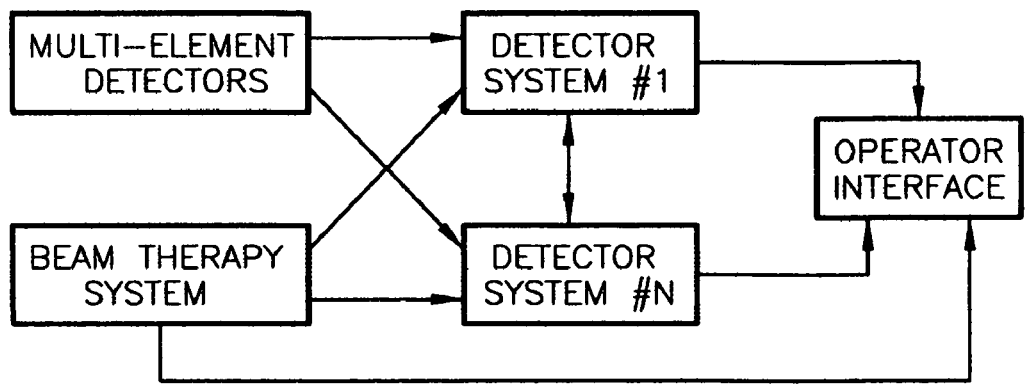
FIG. 2 is a multi-detector system data flow diagram.
Figure 4:
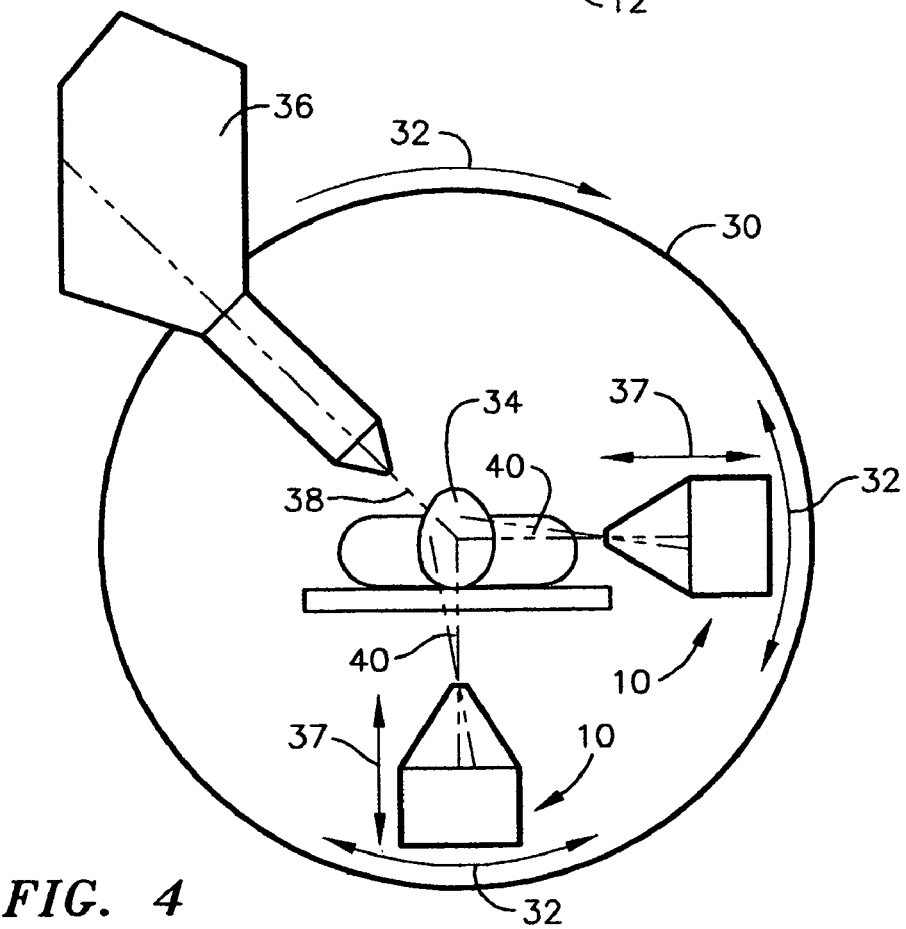
FIG. 4 is shows an example of a two-detector module imaging setup providing two stereotactic views of the beam to enable dynamic 3D localization of the beam position in accordance with the present invention.

The basic preferred operating mode involves two imaging modules, each equipped with a single pinhole and providing two independent views enabling following and monitoring of the beam in 3D. Such an apparatus is depicted schematically in FIG. 4. As shown in FIG. 2, to two detector modules 10 mounted on a gantry 30 that allows rotation of detector modules 10 about the body of a patient/target 34 being subjected to radiation treatment (beam 38) via apparatus 36 as shown by arrows 32, and secondary radiation 40 is detected by detector modules 10, as described above. Detector modules 10 can also be moved closer to or further from patient/target 34, i.e. radially, as indicated by arrows 37. Stereotactic projections of beams 40 require proper opening angle, typically from 15 to 165 degree, to provide good 3D reconstruction of the beam position. A good example of such an angle is 90 degrees where both views are symmetrical and complementary as shown in Accompanying FIG. 4. The process flow for operation of such a multi-detector module system is shown in FIG. 2. As seen in this Figure, interactive feedback between the beam therapy system and the detector system constitutes a preferred arrangement.

As previously described more briefly in connection with FIG. 1, the detector system 10 of the present invention operates as follows: a detector containing multi-element photon sensors converts the incoming photon(s) to electronic signals. Electronic signals from the sensors are processed by a front-end electronics system. The processed electronic signals are transmitted to the data acquisition (DAQ) and computing systems. The location, energy, and arrival time of the incoming photon(s) are determined by the front-end electronics and DAQ/computing system. The DAQ/computing system derives detector images, collects the images, and generates a true image in real time for storage and display on the operator interface. The detector system functions may occupy one or more physical devices. The beam therapy system may interact with the detector system to synchronize timing, co-register images or, obtain position information from the detector system as shown diagrammatically in FIG. 3.

Readout electronics 22: receive, process and transmit the signals from each element of a multi-element sensor. Encode the signals from several sensor elements into a smaller number of electronic signals. Process and transmit the energy of the incoming photon(s). Process and transmit the arrival time of the incoming photon(s).

The DAQ system hardware may: comprise one or more channels of analog-to-digital converters; comprise one or more control and computing elements such as a field-programmable gate array, digital signal processor, microcontroller, or microprocessor; include one or more leading-edge discriminators or constant-fraction discriminators; and synchronize with other devices in the detector or beam therapy systems.

According to various preferred embodiments of the present invention, the DAQ/computing system: receives and processes signals from each sensor element. Receives and processes signals encoded by the front-end electronics system; processes energy data transmitted by the front-end electronics system; receives and processes the arrival time transmitted by the front-end electronics system; computes the position, energy, and arrival time of the incoming photon(s); synchronizes with other devices in the detector system or beam therapy system; collects and stores incoming information from the front-end electronics system; collects and stores computed information; produces a detector image from collected information; collects and stores detector images; collects and stores detector images accumulated during a predetermined time interval; derives and records the arrival time of the detector image collection; computes the true location of the radiation sources within the beam therapy target volume; and collects and stores true radiation source locations.

The DAQ/computing system may acquire and process information from multiple separate detectors. In a multi-detector system, the detector system depicted in FIG. 2; comprises separate systems for each detector; shares the system functional elements among multiple detectors; synchronizes multiple DAQ/computing systems to each other; synchronize one or more DAQ/computing systems to the beam therapy system; merges images or image collections from multiple DAQ/computing systems; merges images or image collections from the DAQ/computing systems and the beam therapy system; and produces a composite, tomographic, or approximate 3D image from multiple detectors viewing the same radiation beam target volume.

Among the functions that may be incorporated into the operator interface are: reception of the raw, computed, or true images from the DAQ/computing system; interaction with the DAQ/computing system to exchange calibration and configuration data; interaction with the beam therapy system; and display of individual detector images, computed images, composite or 3D images, on a single-frame basis or in real-time.

There has thus been described apparatus and a method for monitoring and imaging radiotherapy beams on a real time or delayed basis.

As the invention has been described, it will be apparent to those skilled in the art that the same may be varied in many ways without departing from the intended spirit and scope of the invention, and any and all such modifications are intended to be included within the scope of the appended claims.

What is claimed is:

1. A system for monitoring and imaging low energy radiation generated in the course of radiation therapy comprising:

A radiation treatment apparatus for the application of radiation therapy to a patient wherein said radiation treatment apparatus utilizes a dynamically moving or scanning radiotherapy beam; and a system for detecting secondary low energy radiation emitted from an area of treatment comprising:

I) a gantry for location about a patient being subjected to radiation therapy; and II) rotatably and radially movably mounted on the gantry at least two angularly disposed detector modules each comprising:
   a) a radiation shielding housing;
   b) a low energy pinhole collimator in the radiation shielding housing;
   c) a low energy radiation sensitive layer in the radiation shielding housing behind the pinhole collimator;
   d) a photodetector optically connected to the radiation sensitive layer that registers radiation detection events;
   e) electronics that receive the registered radiation detection events from the photodetector and convert the radiation detection events into dynamic images of a radiation beam entering the housing via the pinhole collimator; and
   f) electronics for converting the dynamic images into spatially resolved images of the radiation detection events on a real time basis.

2. The system for monitoring and imaging low energy radiation of claim 1 wherein said low energy radiation comprises bremsstrahlung radiation.

3. The system for monitoring and imaging low energy radiation of claim 1 wherein said low energy radiation comprises X-ray radiation.

4. The system for monitoring and imaging low energy radiation of claim 1 wherein said low energy radiation comprises Compton scattered gamma radiation.

* * * * *